United States Patent

Umezawa et al.

[11] Patent Number: 4,529,542
[45] Date of Patent: Jul. 16, 1985

[54] PROTEINOUS SUBSTANCE KUD-PC AND ITS PRODUCTION

[75] Inventors: Iwao Umezawa, Tokyo; Kanki Komiyama, Yokohama, both of Japan

[73] Assignee: The Kitasato Institute, Tokyo, Japan

[21] Appl. No.: 506,442

[22] Filed: Jun. 21, 1983

[51] Int. Cl.$^3$ .............................. C07G 7/00
[52] U.S. Cl. ................. 260/112 R; 435/68; 435/822; 435/907; 424/115; 424/116; 424/118; 424/123
[58] Field of Search ............ 260/112 R; 435/68, 822, 435/907; 424/115, 116, 118, 123

[56] References Cited

U.S. PATENT DOCUMENTS

| | | | |
|---|---|---|---|
| 3,709,783 | 1/1973 | Tanaka et al. | 435/68 |
| 4,112,071 | 9/1978 | Bradner et al. | 435/907 |
| 4,147,774 | 4/1979 | Umezawa et al. | 424/116 |
| 4,293,546 | 10/1981 | Nash et al. | 435/109 |

Primary Examiner—John Kight
Assistant Examiner—Garnette D. Draper
Attorney, Agent, or Firm—Ladas & Parry

[57] ABSTRACT

A novel proteinous substance KUP-PC, which is produced by culturing proteinous substance KUD-PC producing organisms belonging to the genus Streptosporangium. KUD-PC increases the antitumor activity of the anti-tumor substance, sporamycin.

1 Claim, 5 Drawing Figures

PROTEINOUS SUBSTANCE KUD-PC AND ITS PRODUCTION

DETAILED EXPLANATION OF INVENTION

This invention relates to novel proteinous substance KUD-PC and its production. More particularly, the present invention pertains the novel proteinous substance KUD-PC which is produced by culturing proteinous substance KUD-PC producing microorganism belonging to genus Streptosporangium and increases the antitumor activity.

We had found that a microorganism strain PO-357 belonging to genus Streptosporangium, isolated from soil sample collected at Setagaya-ku, Toky, Japan, produced the antibiotic PO-357 (which has later been designated as Sporamycin) having antibacterial activity against *Staphylococcus aureus* and *Bacillus subtilis* and antitumor activity. The physico-chemical properties of the said substance and taxonomical properties of the producing microorganisms strain were disclosed in Japanese Unexamined Patent Publication No. 53-7601.

We have found that a physiologically active substance, having no antibacterial activity, being electrophoretically differentiated from sporamycin and increasing antitumor activity of antitumor substance, and have designated the said physiologically active substance as the protein KUD-PC.

The novel protein KUD-PC of the present invention (hereinafter designates as KUD-PC) has the following physico-chemical properties.

(a) Elementary analysis: comprising carbon, hydrogen, nitrogen, oxygen and sulfur, C 49.98%, H 7.27%, N 15.23%, S 1.08%, (found after drying at 100° C. for 3 hours in vacuo), (b) Molecular weight: 11500 calculated by comparison with standard substances (standard polypeptide or standard protein of molecular weight 2512–16949) by SDS-polyacrylamide gel electrophoresis.

(c) Melting point: 258°–260° C. (decomp.), (d) Specific rotation: $[\alpha]_D^{20} = -55.8°$ (c=1.0, HO)

(e) Ultraviolet absorption spectrum: UV spectrum of KUD-PC in aqueous solution and 0.1N-NaOH is shown in FIG. 1.

$\lambda_{max}^{H2O}$: 253, 259, 265, 268 (shoulder), 275, 280 (shoulder) nm, $\lambda_{max}^{0.1N\ NaOH} = 294$ nm, (f) Infrared absorption spectrum: FIG. 2 (KBr), (g) Solubility: soluble in water, and insoluble in common organic solvent such as alcohol, acetone and benzene, (h) Color reaction: positive; Folin-Lowry, biuret and Rydon-Smith reactions, negative; phenol-$H_2SO_4$ and anthron-$H_2SO_4$ reactions, positive for ninhydrin reaction: HCl-hydrolysate, (i) Color and crystalline form: colorless crystals, crystals obtained by ultrafiltration of aqueous solution is hexagonal system crystals and by ammonium sulfate salting-out is prismic, (j) Nature: pH 4–8 (0.1% aqueous solution of KUD-PC), (k) Amino acid analysis: KUD-PC (5 mg) is hydrolysed by HCl in a sealed tube and analysed by liquid chromatography (Hitachi Model 034-2U),

| amino acid | (μM) |
|---|---|
| aspartic acid | 0.144 |
| threonine | 0.258 |
| serine | 0.226 |
| glutamic acid | 0.141 |
| proline | 0.111 |
| glycine | 0.250 |
| alanine | 0.363 |
| valine | 0.265 |
| isoleucine | 0.016 |
| leucine | 0.117 |
| methionine | — |
| tyrosine | 0.020 |
| phenylalanine | 0.079 |
| lysine | 0.089 |
| arginine | 0.040 |
| histidine | (trace) |

(l) Electrophoresis: Electrophoretic profile analysed by SDS-polyacrylamide gel electrophoresis and drawn by chromato-scanner (Shimazu CS-910) is shown in FIG. 3, as a single substance.

Electrophoretic pattern by cellulose-acetate membrane electrophoresis (Cellulo gel RS, pH 2, 1M acetate-formate buffer, 200 V, 1 hour, amido black 10B staining) is shown in FIG. 4, as a single band.

An object of the present invention is to provide a novel proteinous substance KUD-PC having the physico-chemical properties hereinabove.

Another object of the present invention is to provide a process for production of novel proteinous substance KUD-PC which comprises culturing the proteinous substance KUD-PC producing microorganism belonging to genus Streptosporangium, accumulating KUD-PC in a cultured mass and isolating the thus imparted KUD-PC therefrom.

KUD-PC producing strain belongs to genus Streptosporangium as described hereinabove, and the strain PO-357 belonging to genus Streptosporangium isolated by the present inventors are only illustrative for use effectively in the present invention.

Taxonomical properties of the strain are as follows.

1. Morphological properties.

Microscopic examination revealed that the aerial mycelium is straight with most sporangia on the top of the mycelium. Size of sporangium is 5–10μ, mean 7.5μ in diameter. Length of sporangia bearing serial hyphae is short and mostly about 3μ. Spores are round or ovoid with a smooth surface and a diameter of 0.9–1.4μ. Flagella are not observed.

2. Cultural characteristics on various media.

Observation at 27° C., 10–14 days cultivation.

| Medium | Growth | Reverse | Aerial mycelium | Soluble pigment |
|---|---|---|---|---|
| Sucrose-nitrate agar | poor | pale orange | milk white | none |
| Glucose-asparagine agar | poor | pale yellow | milk white | none |
| Glycerol-asparagine agar | poor | pale yellow | milk white | none |
| Inorganic salt-starch agar | poor | brownish white-white | milk white | none |
| Tyrosine agar | moderate | pale orange | pale orange | none |
| Nutrient agar | moderate-good | orange | orange | none |
| Yeast extract-malt extract agar | good | orange | orange | none |
| oatmeal agar | good | dark orange | dark orange | none |

3. Physiological properties.
   (1) Growth temperature: possible at 43° C., optimum growth at about 27°–30° C.
   (2) Melanin production: negative on tyrosine agar.
   (3) Liquefaction of gelatine: positive.
   (4) Hydrolysis of starch: positive.
   (5) Peptonization of milk: positive.
   (6) $H_2S$ formation: negative.
   (7) Nitrate reduction: positive.
4. Utilization of carbon source.
   Observed on Pridham Gottlieb agar medium containing 0.05% of yeast extract.
   Utilization: D-glucose, L-arabinose, D-xylose, D-mannose.
   probable utilization: D-galactose, D-raffinose, L-rhamnose, D-fructose.
   No utilization: inositol, saccharose.
5. Cell wall composition.
   Analysis of cell walls was made by the method of Becker et al. [Appl. Microbiol., 13, 236–243 (1965)].

| DAP* | glycine | arabinose | galactose |
| --- | --- | --- | --- |
| meso type | —** | — | — |

*diaminopimelic acid
**—: not detected.

Various taxonomic properties hereinabove clearly reveal a strain PO-357 as a microorganism belonging to genus Streptosporangium.

Among known species, *Streptosporangium pseudovulgalae* Nonomura [J. Ferm. Tech. Japan, 47, 701–709 (1969)] is closely related to the strain PO-357, but there are differences, especially in the color of the aerial mycelium and in their biological activities. Thus, strain PO-357 is designated as *Streptosporangium pseudovulgalae* PO-357. The strain was deposited in the Institute for Microbial Industry, Agency of Industrial Science and Technology and assigned deposit number FERM-P No. 3571.

In this invention, not only Streptosporangium sp. PO-357 but also the natural or artificial mutants thereof, obtained by ultraviolet, X-ray, radiation or chemical mutagens, as well as the microorganisms belonging to genus Streptosporangium having novel proteinous substances KUD-PC producing activity, can be utilized in the production of KUD-PC.

In the present invention, KUD-PC producing microorganisms belonging to genus Streptosporangium is cultured in a conventional medium. The cultivation can be carried out in the conventional medium, in general, for Streptomyces. As for the medium, a nutrient medium comprising assimirable carbon and nitrogen sources and inorganic salts can be used. As for assimirable carbon sources, glucose, sucrose, molasses, starch, dextrin, glycerin and organic acid are used individually or in combination. As for nitrogen sources, peptone, meat extract, yeast extract, dry yeast, soy bean powder, corn steep liquor, cottonseed cake, caseine, soy bean protein hydrolysate, amino acids and urea are used individually or in combination. If required, inorganic salt such as sodium, potassium, calcium, magnesium or phosphate salts is added. Further, trace nutrient elements or growth stimulants which accelerate growth of the microorganisms or production of KUD-PC can optionally be added.

Cultivation can preferably be performed at an aerobic condition such as shaking culture or submerged aeration culture at neutral pH at 27°–30° C. for 40–72 hours.

KUD-PC is produced in a cultured broth. Cultivation should preferably be terminated at highest accumulation of KUD-PC in a cultured broth. Cultivation conditions such as culture composition, pH, temperature, aggitation and aeration can be selected depending upon strain used and other conditions. Anti-foaming agent such as silicon oil, vegetable oil or surface active agents can be added if necessary.

Since KUD-PC imparted in the thus obtained cultured broth is mainly found in a cultured broth, KUD-PC can preferably be isolated from culture filtrate separated by filtration or centrifugation after optionally adding filter-aid. Isolation of KUD-PC from culture filtrate can be performed by applying the nature of KUD-PC in which the KUD-PC is soluble in water and insoluble in organic solvent such as alcohol, acetone or benzene. Generally, a conventional isolation and purification methods for protein or polypeptide can be applied. Salting-out by ammonium sulfate or ammonium chloride, fractional precipitation by methanol, ethanol or acetone, ion-exchange chromatography using ion-exchanger, ion-exchange cellulose or ion-exchange Sephadex, adsorption chromatography using active-carbon, silica-gel, alumina, hydroxyapatite, cellulose or adsorption resin such as HP-10 resin, gel-filtration chromatography using Sephadex or Biogel, electrophoresis, counter current distribution, dialysis, ultrafiltration or concentration procedure can be applied individually or in combination thereof, or repeatedly. Elution of chromatography can be carried out by water, aqueous alcohol, aqueous acetone, buffer or aqueous solution of inorganic or organic salt.

An embodiment of the isolation and purification procedures for KUD-PC is illustrated in details hereinbelow.

Cultured broth, added with filter-aid, is filtered to remove mycelia. Ammonium sulfate is added to culture filtrate at 90% saturation under cooling at neutral pH. Salting-out precipitate was collected by filtration or centrifugation and dissolved in water or neutral buffer solution. The solution is dialysed under cooling or subjected to ultrafiltration using semipermeable membrane for desalting. Example of semipermeable membrane is synthetic semi-permeable membrane, which cut-off the molecular weight below 1,000 and over 10,000, such as UH-L, UK-10 (product of Toyo Roshi Co., Tokyo).

De-salting solution is passed through a column of ion-exchange cellulose or ion-exchange Sephadex after washing with water to elute by elution solvent.

Examples of ion-exchange cellulose are DEAE-cellulose, ECTEOLA-cellulose, SE-cellulose and CM-cellulose.

The above ion-exchange cellulose or ion-exchange Sephadex is preferably bufferized with previously setting dilution concentration buffer solution. Elution liquid is a buffer of inorganic or organic salt. Example of inorganic salt is sodium chloride, potassium chloride, ammonium chloride, ammonium sulfate or phosphate salt and that of organic salt is sodium acetate or sodium formate, with 0.01–1M/l. Example of buffer solution is phosphate, acetate, citrate or trishydroxymethylamino methane buffer. A pH of buffer solution is pH 5–8, preferably at neutral pH at concentration of 0.001–0.5M/l. In the elution process hereinabove, concentrations of inorganic or organic salts and buffer solution, and pH may optionally be changed gradiently or continuously.

Concentration or de-salting is performed by ammonium sulfate salting-out, ultrafiltration or dialysis. Purification of concentrated or de-salted solution of KUD-PC is preferably performed by gel-filtration chromatography. Example of gel-giltrating agent is Biogel P-10, Biogel P-30 or Sephadex G-75 (trade names). Elution is carried out with water or buffer solution.

KUD-PC can be crystallized from the thus highly purified solution of KUD-PC. For example, highly purified eluate solution of KUD-PC by ion-exchange chromatography and/or gel-filtration chromatography is treated by ultrafiltration concentration and/or ammonium sulfate precipitation to obtain the crystalline KUD-PC. If not crystallized, KUD-PC can be isolated by further chromatography or lyophilization procedure.

Biological properties of KUD-PC are as follows:

(1) Antimicrobial action:

KUD-PC does not show antibacterial action on test organisms such as *Staphylococcus aureus, Bacillus subtilis* and *Bacillus cereus.*

(2) Cytoclasis action:

Cytoclasis (cytotoxic) action of KUD-PC is shown in Table 1, in which KUD-PC has strong cytoclasis activity on BHK-cells.

TABLE 1

| KUD-PC | sporamycin | $^3$H-TdR | $^3$H-UR | Protein |
|---|---|---|---|---|
| 0 μg/ml | 25 U/ml | 4 | 21 | 22 |
| 0 | 5 | 5 | 24 | 23 |
| 0 | 10 | 55 | 30 | 42 |
| 0.1 | 2.5 | 27 | −13 | 22 |
| 1 | 2.5 | 26 | −27 | 28 |
| 10 | 2.5 | 42 | 0 | 17 |
| 0.1 | 5 | 49 | 14 | 42 |
| 1 | 5 | 34 | −3 | 30 |
| 10 | 5 | 33 | −12 | 23 |
| 0.1 | 10 | 84 | 43 | 52 |
| 1 | 10 | 68 | 44 | 41 |
| 10 | 10 | 42 | 5 | 30 |

(3) Antitumor activity:

(1) Experimental method:

(i) Sarcoma 180, $1 \times 10^5$ cells, are inoculated subcutaneously in ddY mice. After 3 days mixture of sporamycin and KUD-PC is administered intraveneously. Further KUD-PC is administered intraveniously at day 4, 5 and 6 to observe life-prolongation effects.

(ii) Effect against Ehrlich ascites carcinoma: Ehrlich ascites carcinoma, $2.5 \times 10^6$ cells, are inoculated intraperitoneally in ddy Mice (5 mice in one group, 5 weeks age). On next day, mixture of sporamycin and KUD-PC is administered intraperitoneally to observe life-prolongation days.

(2) Evaluation:

$$\frac{treated}{non\text{-}treated} \times 100 - 100 = \text{life-prolongation ratio (\%)}$$

(3) Combination effect of KUD-PC and sporamycin against animal transplantable carcinoma, Ehrlich ascited carcinoma is shown in Table 2-1 and -2, in which KUD-PC increases an antitumor activity of sporamycin.

(4) Toxicity:

Acute toxicity ($LD_{50}$) of KUD-PC is as follows.
mice i.p. $LD_{50} > 2000$ mg/kg
mice i.v. $LD_{50} > 2000$ mg/kg Following examples illustrate the present invention but are not construed as limiting.

EXAMPLE 1

One loopful microorganisms from slant culture of *Streptosporangium pseudovulgalae* PO-357, FERM-P No. 3571 was inoculated into liquid medium A comprising glucose 2.0%, dry yeast 0.3%, peptone 0.5%, meat extract 0.5%, calcium carbonate 0.3% and sodium chloride 0.5%, (pH 7.0, 100 ml) in 500 ml Sakaguchi flask, and shake cultured at 70 r.p.m. at 27° C. for 72 hours. This seed culture (10 ml) was inoculated into medium B comprising glucose 0.2%, starch 1.5%, dry yeast 0.15%, peptone 0.23%, meat extract 0.3% and calcium carbonate 0.25% (100 ml, pH 7.0) in ten flasks of 500 ml Sakaguchi flssks, and shake cultured at 170 r.p.m. at 27° C. for 48 hours. The cultured second seed (1 lit.) was inoculated into medium A (130 lit.) in 200 lit. stainless steel tank, and submerged aeration cultured at aeration 100 lit./min., agitation 250 r.p.m., inner pressure 0.5 kg/cm$^2$, at 28° C. for 72 hours. KUD-PC was detected by cellulose acetate membrane electrophoresis in the cultured broth. The cultured broth (115 lit.) was cooled below 5° C., added Hyflosupercel (trade name) (2.3 kg) and filtered by filter press. Filtered mycelia were washed with water, combined with the filtered broth, which was cooled below 5° C., then added Hyflosupercel (400 g) therein, and added ammonium sulfate (82.5 kg) up to 90% ammonium sulfate saturation. The mixture was stirred at below 5° C. for 1 hour, and the thus obtained precipitate was collected to obtain wet solid material (900 g). Following operations were carried out in a dark room at below 5° C.

The above solid material was dissolved in water (3 lit.), filtered to remove insoluble material and washed with water. Filtrate and washing solution was combined (total 4 lit.). Ammonium sulfate (2.5 kg) was added thereto to prepare 90% saturation of ammonium sulfate, stirred for 1 hour and filtered the sedimentate to obtain the precipitated material (102 g), which was dissolved in water (450 ml). The solution was dialysed with cellophane tube against de-ionized water (30 lit.) for 3 days. De-ionized water was replaced one in an every day. The thus obtained de-salted solution (1170 ml) was charged on a column (9 × 50 cm) of DEAE-cellulose (product of Brown Co., U.S.A., granule type), previously bufferized with 0.002M phosphate buffer (pH 7.5–8.0). Elution was carried out 0.002M phosphate buffer (pH 7.4, 6.4 lit.) and 0.01M phosphate buffer (pH 7.4, 5 lit.), in this order, to fractionate each 30 ml fraction. Each fraction was checked by Folin-Lawry protein detection method and bioassay using *Staphylococcus aureus* 209P, and found KUD-PC in fractions No. 181–300 and sporamycin in fractions No. 321–400. Fractions containing KUD-PC were collected (3.8 lit.) and ammonium sulfate was added therein to prepare 40% saturation of ammonium sulfate, then filtered off the precipitate formed within one hour. Ammonium sulfate was added to the filtrate to prepare 90% saturation, stirred for 1 hour and collected the precipitate, which was fissolved in water. The solution (78 ml) was charged on a column (6.0 × 62 cm) of Biogel P-30 (trade name, Biorad Laboratories Co.), eluted with water for gel-filtration and fractionated the eluted each fraction (20 g). Each fraction was checked by protein detection and bioassay as hereinabove explained to obtain fractions No. 41–54 (280 ml). The combined fractions were concentrated up to 10 ml by ultrafiltration membrane UH-1, and allowed to stand for overnight under cooling. Precipitated crystals were filtered, washed with small amount of water and dried to obtain hexagonal system colorless crystals of KUD-PC (120 mg). m.p. 258°–260° C. (decomp.).

The first mother liquor and washing solution were combined, added ammonium sulfate up to 25% saturation and allowed to stand for 3 days under cooling in a dark room. Precipitated crystals were filtered, washed with small amount of cold water and dried to obtain prismic colorless crystals of KUD-PC (770 mg). The second mother liquor and washing solution were combined and ammonium sulfate was added therein up to 30% saturation to obtain crystals (560 mg). Further the third mother liquor was treated with ammonium sulfate up to ammonium sulfate 60% saturation to obtain crystals (450 mg). The thus obtained hexagonal system colorless crystals and prismic crystals were subjected to electrophoresis with cellulose acetate membrane (CHEMETRON Co., Cellulogel RS, 5×12 cm) (1M acetate-formate buffer, pH 2, 200 V, 1 hour, stained by Amide Black 10 B). As shown in FIG. 4, single identical bands were found in the same position. Electrophoretic profile of SDS-polyacrylamide gel electrophoresis of hexagonal system colorless crystals is shown in FIG. 3 (scanned by scanner, Shimazu CS-910), in which single band is found.

EXAMPLE 2

Main cultrued broth (116 lit.) obtained by the same process as shown in example 1 was treated by the same way as of in example 1 to obtain de-salted solution (1080 ml). The solution was charged on a column (9×50 cm) of DEAE-cellulose, previously bufferized by 0.002M phosphate buffer (pH 7.0–7.4), purified by the same process as in example 1 to obtain KUD-PC and sporamycin containing fractions No. 121–260. The fractions were combined and treated by the same way as in example 1 for ammonium sulfate saturation 90% and Biogel P-30 column chromatography to obtain KUD-PC in the fraction No. 41–50 and sporamycin in the fraction No. 53–64. Biogel P-30 column chromatographic pattern is shown in FIG. 5. The fractions containing KUD=PC were treated by ultrafiltration and crystallization as the same as in example 1 to obtain hexagonal system colorless crystals (730 mg) [m.p. 258°–260° C. (decomp.)], prismic crystals (1.48 g) and crystals (0.9 g). These crystals were found with single band at the same electrophoretic position by cellulose acetate membrane electrophoresis.

EXAMPLE 3

Main cultured broth obtained by the same process as in example 1 was purified by the same way as in example 1 to obtain ammonium sulfate saturation 40–90% precipitate of fractions containing KUD-PC by DEAE-cellulose column chromatography. The precipitate was dissolved in water (70 ml), and charged on a column (6×78 cm) of Sephadex G-50, previously swollen with water, for gel-filtration chromatography. Eluate by water was fractionated each 20 g fraction. Each fraction was checked by protein detection to obtain fractions No. 56–80 containing KUD-PC. The solution was desalted and concentrated by ultrafiltration, and the concentrate (100 ml) was lyophilized to obtain white powder KUD-PC (1.45 g).

The product showed single band by cellulose acetate membrane electrophoresis and confirmed the same substance as of hexagonal system colorless crystals and prismic crystals obtained in example 1.

EXAMPLE 4

In example 1, fermentation in 200 lit. tank was carried out for 96 hours to obtain main culture broth (114 lit.). KUD-PC was detected in the broth by cellulose acetate membrane electrophoresis and sporamycin did not found by bioassay.

The main culture broth was purified by the same process as in example 1 to obtain hexagonal system colorless crystals (50 mg) [m.p. 258°–260° C. (decomp.)] and prismic crystals (1.89 g). These crystals were shown single band by cellulose acetate elextrophoresis.

TABLE 2-1

| sample | | life-prolongation ratio (%) | number of mice >60 days life-prolongation |
|---|---|---|---|
| KUD-PC | sporamycin | | |
| 0 mg/kg | 0 U/kg | 0% | 0/7 |
| 2.5 | 0 | 10 | 0/7 |
| 10 | 0 | 13 | 0/7 |
| 0 | 3.000 | 35 | 0/7 |
| 2.5 | 3.000 | 65 | 2/7 |
| 10 | 3.000 | 70 | 3/7 |
| 0 | 6.000 | 43 | 1/7 |
| 2.5 | 6.000 | >161 | 5/7 |
| 10 | 6.000 | >161 | 4/7 |

TABLE 2-2

| sporamycin (U/kg) | KUD-PC (mg/kg) | number of intermediate life-prolongation days. | life-prolongation ratio (%) |
|---|---|---|---|
| — | — | 21 | 0 |
| 1500 | 10 | 33 | 57 |
| | 2.5 | 29 | 38 |
| | 0.63 | 38 | 81 |
| | 0.15 | 32 | 52 |
| | — | 29 | 38 |
| 750 | 10 | 27 | 29 |
| | 2.5 | 33 | 57 |
| | 0.63 | 45 | 114 |
| | 0.15 | 32 | 52 |
| | — | 26 | 24 |
| 188 | 10 | 23 | 10 |
| | 2.5 | 25 | 19 |
| | 0.63 | 43 | 105 |
| | 0.15 | 37 | 76 |
| | — | 25 | 19 |

Figure 1:
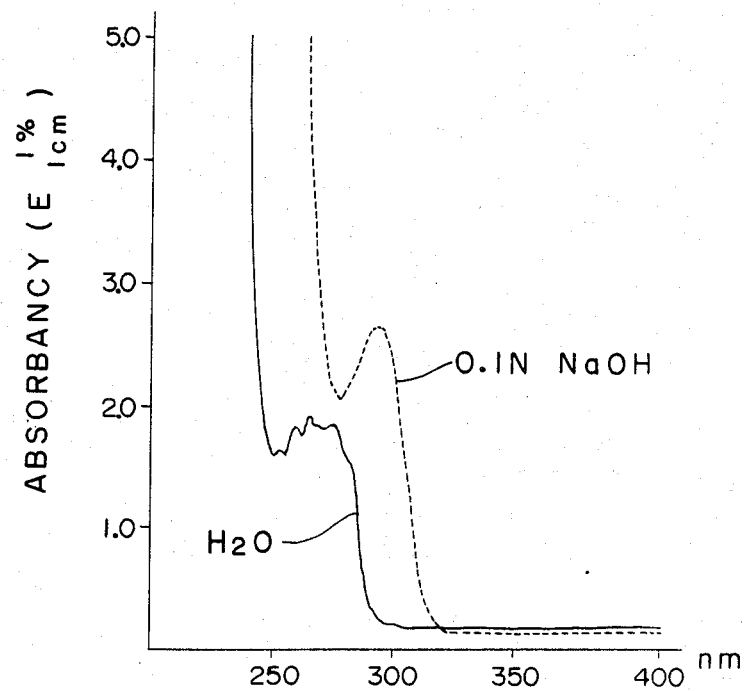
FIG. 1: UV spectrum of KUD-PC.
Figure 2:
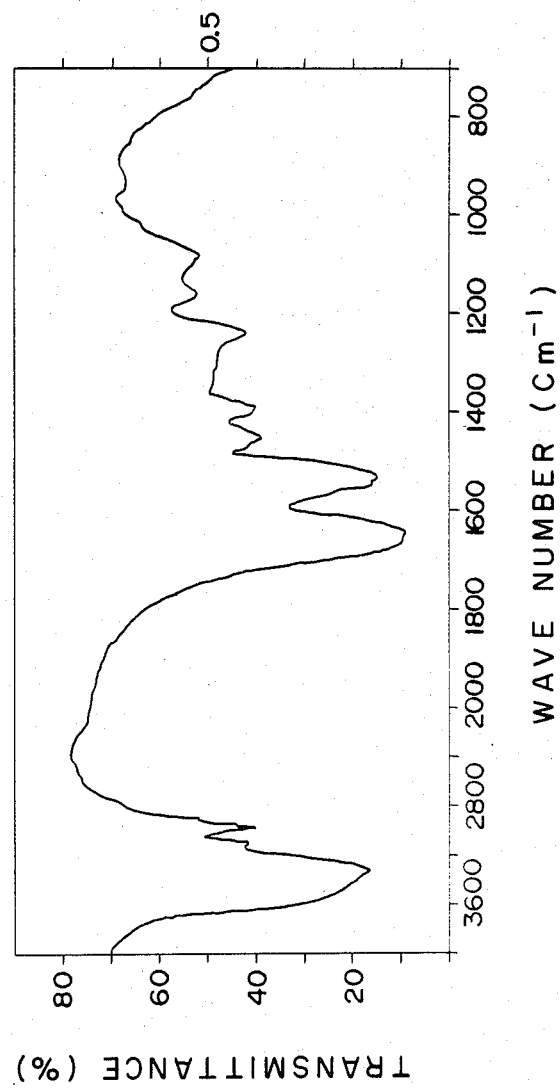
FIG. 2: IR spectrum of KUD-PC.

We claim:

1. A novel protein KUD-PC having the following physicochemical properties:
   (A) Elementary analysis: comprising carbon, hydrogen, nitrogen, oxygen and sulfur; C 49.98%, H 7.27%, N 15.23%, S 1.08%,
   (B) Molecular weight: 11,500 (SDS-polyacrylamide gel electrophoresis),
   (C) Melting point: 258°–260° C. (decomp.),
   (D) Specific rotation: $[\alpha]_D^{20} = -55.8°$ (c=1.0, H$_2$O),
   (E) Ultraviolet absorption spectrum: as shown in FIG. 1,
   (F) Infrared absorption spectrum: as shown in FIG. 2, (G) Solubility: soluble in water, insoluble in organic solvent (alcohol, acetone and benzene), (H) Color reaction: positive: Folin-Lowry, biuret and Rydon-Smith reactions, negative: phenol-$H_2SO_4$ and anthrone-$H_2SO_4$ reactions, HCl hydrolysate: positive for ninhydrin reaction, (I) Nature: pH 4-8 in 0.1% aqueous solution, (J) Color and crystalline form: colorless crystals, (K) Amino acid composition: Molar ratio of amino acid analysis of HCl hydrolysate is as follows;

| | |
|---|---|
| aspartic acid | 0.144 |
| threonine | 0.258 |
| serine | 0.226 |
| glutamic acid | 0.141 |
| proline | 0.111 |
| glycine | 0.250 |
| alanine | 0.363 |
| valine | 0.265 |
| isoleucine | 0.016 |
| leucine | 0.117 |
| methinine | — |
| tyrosine | 0.020 |
| phenylalanine | 0.079 |
| lysine | 0.089 |
| arginine | 0.040 |
| histidine | (trace) |

Figure 3:
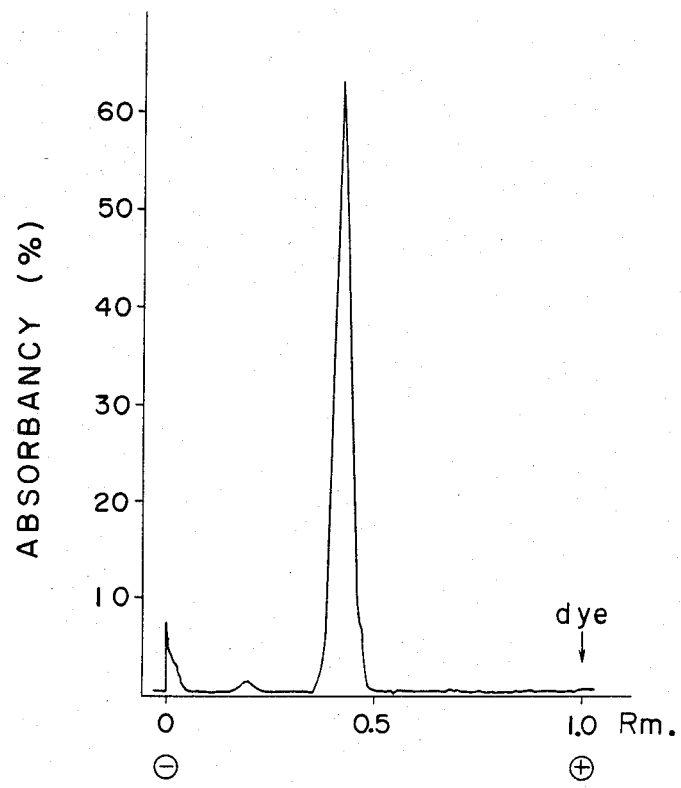
FIG. 3: Electrophoretic profile of KUD-PC by SDS-polyacrylamide gel electrophoresis.
Figure 4:
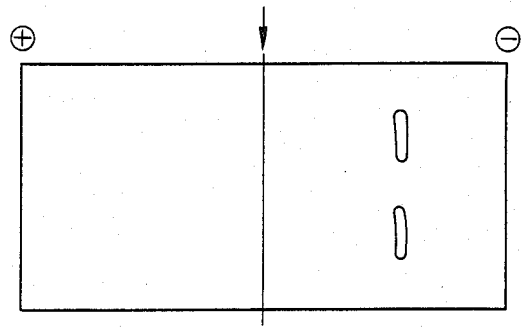
FIG. 4: Cellulose acetate membrane electrophoresis of KUD-PC.
Figure 5:
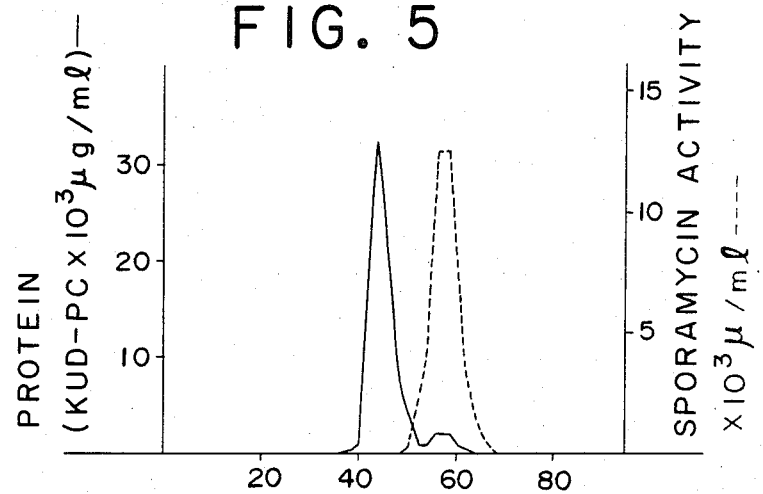
FIG. 5: Biogel P-30 column chromatography of KUD-PC and sporamycin.

(L) Electrophoresis: Electrophoretic profile of SDS-polyacrylamide gel electrophoresis is shown in FIG. 3 and the substance shows single peak.

* * * * *